(12) United States Patent
Schnorr et al.

(10) Patent No.: US 8,846,340 B2
(45) Date of Patent: Sep. 30, 2014

(54) CARBOHYDRATE-BINDING MODULES OF A NEW FAMILY

(75) Inventors: Kirk Matthew Schnorr, Holte (DK); Lars Lehmann Hylling Christensen, Allerod (DK)

(73) Assignee: Novozymes A/S, Bagsvaerd (DK)

( * ) Notice: Subject to any disclaimer, the term of this patent is extended or adjusted under 35 U.S.C. 154(b) by 960 days.

(21) Appl. No.: 10/576,528

(22) PCT Filed: Oct. 26, 2004

(86) PCT No.: PCT/DK2004/000734
§ 371 (c)(1),
(2), (4) Date: Apr. 19, 2006

(87) PCT Pub. No.: WO2005/042735
PCT Pub. Date: May 12, 2005

(65) Prior Publication Data
US 2007/0072185 A1  Mar. 29, 2007

Related U.S. Application Data

(60) Provisional application No. 60/515,927, filed on Oct. 30, 2003.

(30) Foreign Application Priority Data

Oct. 30, 2003 (DK) .................. 2003 01607

(51) Int. Cl.
| | | |
|---|---|---|
| C12N 9/42 | (2006.01) | |
| C12N 9/24 | (2006.01) | |
| C12N 1/00 | (2006.01) | |
| D06M 16/00 | (2006.01) | |
| C02F 3/34 | (2006.01) | |
| C12P 39/00 | (2006.01) | |
| C07K 14/37 | (2006.01) | |

(52) U.S. Cl.
CPC .............. *C07K 14/37* (2013.01); *C12N 9/2434* (2013.01)
USPC ............... 435/42; 435/209; 435/193; 435/43; 435/69.1; 435/254.1; 435/6.1; 435/263; 435/483; 435/162; 435/262; 530/396; 536/23.5

(58) Field of Classification Search
None
See application file for complete search history.

(56) References Cited

FOREIGN PATENT DOCUMENTS

| | | |
|---|---|---|
| WO | WO 03/000941 | 1/2003 |
| WO | WO 03/044049 | 5/2003 |

OTHER PUBLICATIONS

Coutinho et al., Recent Advances in Carbohydrate Bioengineering, "Carbohydrate-Active Enzymes: An Integrated Database Approach", pp. 3-12 (1999).
Bourne et a., Carbohydrates and Glycoconjugates, "Glycoside Hydrolases and Glycosyltransferases: families and functional modules", pp. 593-600 (2001).
Levy et al., Biotechnology Advances, vol. 20, pp. 191-213 (2002).
Blume et al., The Journal of Biological Chemistry, vol. 266, No. 23, pp. 15432-15437 (1991).
Banka et al., World J Microbiol Biotechnology, vol. 14, 551-558 (1998).
Gao et al., Acta Biochim Biophysics, vol. 33, pp. 13-18 (2001).
Gikes et al., Int J Biol Macromol, vol. 15, pp. 347-351 (1993).
Krull et al., Biotechnol Biotengg, vol. 31, pp. 321-327 (1988).
Tomme et al., FEBS Lett, vol. 243, pp. 239-243 (1989).
Tomme et al., Enzy Degrad Insoluble Polysac, pp. 142-163 (1995).

*Primary Examiner* — Catherine Hibbert
(74) *Attorney, Agent, or Firm* — Robert L. Starnes

(57) ABSTRACT

The present invention relates to non-catalytic carbohydrate-binding modules (CBM) belonging to a new family of CBM's. A CBM of the invention was found attached to a glycosyl hydrolase family 61 (GH61) polypeptide and was shown to have little homology with known CBM's indicating that it is the first known member of a new family of CBM's. The present invention further relates to CBM's preferably exhibiting binding affinity for cellulose; to a method of producing such CBM's; and to methods for using such CBM's in the textile, detergent and cellulose fiber processing industries, for purification of polypeptides, immobilization of active enzymes, baking, manufacturing of biofuel, modification of plant cell walls.

12 Claims, No Drawings

SEQUENCE LISTING

<160> NUMBER OF SEQ ID NOS: 9

<210> SEQ ID NO 1
<211> LENGTH: 629
<212> TYPE: DNA
<213> ORGANISM: Pseudoplectania nigrella
<220> FEATURE:
<221> NAME/KEY: CDS
<222> LOCATION: (10)..(531)

<400> SEQUENCE: 1

```
gaattcaaa atg gtc aac ttc acc acc ctc ctc ccg gtt ctt gcc gct ctt        51
          Met Val Asn Phe Thr Thr Leu Leu Pro Val Leu Ala Ala Leu
          1               5                   10 att gga gct gcc aat gcc cac act cgt gtc tac gga ctc tcc gtc aac          99
Ile Gly Ala Ala Asn Ala His Thr Arg Val Tyr Gly Leu Ser Val Asn
15                  20                  25                  30 gat gtc aca tcc tcc ggc acc tcc aat gac aag gcc gtc gct tct tcc         147
Asp Val Thr Ser Ser Gly Thr Ser Asn Asp Lys Ala Val Ala Ser Ser
                35                  40                  45 agt att gcg gcc gtg gac cct gtg acc agc tcc gtc gta gcc tct gtt         195
Ser Ile Ala Ala Val Asp Pro Val Thr Ser Ser Val Val Ala Ser Val
            50                  55                  60 cag gtc cct aac ttc act gcc act gac gtc ccc act ttt act gcc acc         243
Gln Val Pro Asn Phe Thr Ala Thr Asp Val Pro Thr Phe Thr Ala Thr
        65                  70                  75 gac atc cct act ttc act gct act gat gtt cct atc ttc acc aag aag         291
Asp Ile Pro Thr Phe Thr Ala Thr Asp Val Pro Ile Phe Thr Lys Lys
    80                  85                  90 ccc caa cag ccc tca act tta ttg acc cgc acc cgt acc cat gcc tct         339
Pro Gln Gln Pro Ser Thr Leu Leu Thr Arg Thr Arg Thr His Ala Ser
95                  100                 105                 110 gtt tca ttc gtc gct aag ccc tcc gct ttt att ccc aag cct tcc gcg         387
Val Ser Phe Val Ala Lys Pro Ser Ala Phe Ile Pro Lys Pro Ser Ala
                115                 120                 125 agc aca atc ccg tca aag ccc aag act ccc gaa gag gtt aat aag tgc         435
Ser Thr Ile Pro Ser Lys Pro Lys Thr Pro Glu Glu Val Asn Lys Cys
            130                 135                 140 ctt gac gct gtc aac gcc tgt att aca cag gcc cag agc tcc att gga         483
Leu Asp Ala Val Asn Ala Cys Ile Thr Gln Ala Gln Ser Ser Ile Gly
145                 150                 155 gga gtt gtc aac ttt gag cct tgc gag agc cag aga gct ctt tgc tat         531
Gly Val Val Asn Phe Glu Pro Cys Glu Ser Gln Arg Ala Leu Cys Tyr
    160                 165                 170 taggaactgc aaagaatctg gggggatggt agcgaggttg agaggtggag gagcggagga       591 gtagggagg tgagatggag taagattaag cggccgca                                629
```

<210> SEQ ID NO 2
<211> LENGTH: 174
<212> TYPE: PRT
<213> ORGANISM: Pseudoplectania nigrella

<400> SEQUENCE: 2

```
Met Val Asn Phe Thr Thr Leu Leu Pro Val Leu Ala Ala Leu Ile Gly
1               5                   10                  15

Ala Ala Asn Ala His Thr Arg Val Tyr Gly Leu Ser Val Asn Asp Val
            20                  25                  30

Thr Ser Ser Gly Thr Ser Asn Asp Lys Ala Val Ala Ser Ser Ser Ile
        35                  40                  45

Ala Ala Val Asp Pro Val Thr Ser Ser Val Val Ala Ser Val Gln Val
```

```
            50                  55                  60
Pro Asn Phe Thr Ala Thr Asp Val Pro Thr Phe Thr Ala Thr Asp Ile
 65                  70                  75                  80

Pro Thr Phe Thr Ala Thr Asp Val Pro Ile Phe Thr Lys Lys Pro Gln
                 85                  90                  95

Gln Pro Ser Thr Leu Leu Thr Arg Thr Arg Thr His Ala Ser Val Ser
            100                 105                 110

Phe Val Ala Lys Pro Ser Ala Phe Ile Pro Lys Pro Ser Ala Ser Thr
        115                 120                 125

Ile Pro Ser Lys Pro Lys Thr Pro Glu Glu Val Asn Lys Cys Leu Asp
130                 135                 140

Ala Val Asn Ala Cys Ile Thr Gln Ala Gln Ser Ser Ile Gly Gly Val
145                 150                 155                 160

Val Asn Phe Glu Pro Cys Glu Ser Gln Arg Ala Leu Cys Tyr
                165                 170

<210> SEQ ID NO 3
<211> LENGTH: 31
<212> TYPE: DNA
<213> ORGANISM: Pseudoplectania nigrella
<220> FEATURE:
<221> NAME/KEY: misc_feature Primer NP887U1
<222> LOCATION: (1)..(31)

<400> SEQUENCE: 3
gacatcgttg acggagagtc cgtagacacg a                               31

<210> SEQ ID NO 4
<211> LENGTH: 34
<212> TYPE: DNA
<213> ORGANISM: Pseudoplectania nigrella
<220> FEATURE:
<221> NAME/KEY: misc_feature Primer NP887D1
<222> LOCATION: (1)..(34)

<400> SEQUENCE: 4
acatcctccg gcacctccaa tgacaaggcc gtcg                            34

<210> SEQ ID NO 5
<211> LENGTH: 21
<212> TYPE: DNA
<213> ORGANISM: Artificial
<220> FEATURE:
<223> OTHER INFORMATION: Primer PNA2I
<220> FEATURE:
<221> NAME/KEY: misc_feature Primer PNA2I
<222> LOCATION: (1)..(21)

<400> SEQUENCE: 5
gtttccaact caatttacct c                                          21

<210> SEQ ID NO 6
<211> LENGTH: 32
<212> TYPE: DNA
<213> ORGANISM: Artificial
<220> FEATURE:
<223> OTHER INFORMATION: Primer NP887Dau1
<220> FEATURE:
<221> NAME/KEY: misc_feature Primer NP887Dau1
<222> LOCATION: (1)..(32)

<400> SEQUENCE: 6
ccaaagcttt tcatcctccg gcacctccaa tg                              32
```

<210> SEQ ID NO 7
<211> LENGTH: 32
<212> TYPE: DNA
<213> ORGANISM: Artificial
<220> FEATURE:
<223> OTHER INFORMATION: Primer N887Dau2
<220> FEATURE:
<221> NAME/KEY: misc_feature Primer NP887Dau2
<222> LOCATION: (1)..(32)

<400> SEQUENCE: 7
gcgaagctta atcttactcc atctcacctc cc				32

<210> SEQ ID NO 8
<211> LENGTH: 573
<212> TYPE: DNA
<213> ORGANISM: Pseudoplectania nigrella
<220> FEATURE:
<221> NAME/KEY: CDS
<222> LOCATION: (1)..(570)
<223> OTHER INFORMATION: Positions 1-57 Candida lipase signal peptide,
      positions 58-147 Candida lipase sequence, positions 148-570 P.
      nigrella CBM polypeptide.

<400> SEQUENCE: 8

| atg | aag | cta | ctc | tct | ctg | acc | ggt | gtg | gct | ggt | gtg | ctt | gcg | act | tgc | 48 |
|---|---|---|---|---|---|---|---|---|---|---|---|---|---|---|---|---|
| Met | Lys | Leu | Leu | Ser | Leu | Thr | Gly | Val | Ala | Gly | Val | Leu | Ala | Thr | Cys | |
| 1 | | | | 5 | | | | | 10 | | | | | 15 | | |

| gtt | gca | gcc | act | cct | ttg | gtg | aag | tgc | gca | act | agt | ggc | cat | tac | ggc | 96 |
|---|---|---|---|---|---|---|---|---|---|---|---|---|---|---|---|---|
| Val | Ala | Ala | Thr | Pro | Leu | Val | Lys | Cys | Ala | Thr | Ser | Gly | His | Tyr | Gly | |
| | | | 20 | | | | | 25 | | | | | 30 | | | |

| ctc | gcg | agg | ccg | cct | cgg | ccc | caa | cga | att | ctt | gga | ata | tta | agc | ttt | 144 |
|---|---|---|---|---|---|---|---|---|---|---|---|---|---|---|---|---|
| Leu | Ala | Arg | Pro | Pro | Arg | Pro | Gln | Arg | Ile | Leu | Gly | Ile | Leu | Ser | Phe | |
| | | 35 | | | | | 40 | | | | | 45 | | | | |

| tca | tcc | tcc | ggc | acc | tcc | aat | gac | aag | gcc | gtc | gct | tct | tcc | agt | att | 192 |
|---|---|---|---|---|---|---|---|---|---|---|---|---|---|---|---|---|
| Ser | Ser | Ser | Gly | Thr | Ser | Asn | Asp | Lys | Ala | Val | Ala | Ser | Ser | Ser | Ile | |
| | 50 | | | | | 55 | | | | | 60 | | | | | |

| gcg | gcc | gtg | gac | cct | gtg | acc | agc | tcc | gtc | gta | gcc | tct | gtt | cag | gtc | 240 |
|---|---|---|---|---|---|---|---|---|---|---|---|---|---|---|---|---|
| Ala | Ala | Val | Asp | Pro | Val | Thr | Ser | Ser | Val | Val | Ala | Ser | Val | Gln | Val | |
| 65 | | | | | 70 | | | | | 75 | | | | | 80 | |

| cct | aac | ttc | act | gcc | act | gac | gtc | ccc | act | ttt | act | gcc | acc | gac | atc | 288 |
|---|---|---|---|---|---|---|---|---|---|---|---|---|---|---|---|---|
| Pro | Asn | Phe | Thr | Ala | Thr | Asp | Val | Pro | Thr | Phe | Thr | Ala | Thr | Asp | Ile | |
| | | | | 85 | | | | | 90 | | | | | 95 | | |

| cct | act | ttc | act | gct | act | gat | gtt | cct | atc | ttc | acc | aag | aag | ccc | caa | 336 |
|---|---|---|---|---|---|---|---|---|---|---|---|---|---|---|---|---|
| Pro | Thr | Phe | Thr | Ala | Thr | Asp | Val | Pro | Ile | Phe | Thr | Lys | Lys | Pro | Gln | |
| | | | 100 | | | | | 105 | | | | | 110 | | | |

| cag | ccc | tca | act | tta | ttg | acc | cgc | acc | cgt | acc | cat | gcc | tct | gtt | tca | 384 |
|---|---|---|---|---|---|---|---|---|---|---|---|---|---|---|---|---|
| Gln | Pro | Ser | Thr | Leu | Leu | Thr | Arg | Thr | Arg | Thr | His | Ala | Ser | Val | Ser | |
| | | 115 | | | | | 120 | | | | | 125 | | | | |

| ttc | gtc | gct | aag | ccc | tcc | gct | ttt | att | ccc | aag | cct | tcc | gcg | agc | aca | 432 |
|---|---|---|---|---|---|---|---|---|---|---|---|---|---|---|---|---|
| Phe | Val | Ala | Lys | Pro | Ser | Ala | Phe | Ile | Pro | Lys | Pro | Ser | Ala | Ser | Thr | |
| | 130 | | | | | 135 | | | | | 140 | | | | | |

| atc | ccg | tca | aag | ccc | aag | act | ccc | gaa | gag | gtt | aat | aag | tgc | ctt | gac | 480 |
|---|---|---|---|---|---|---|---|---|---|---|---|---|---|---|---|---|
| Ile | Pro | Ser | Lys | Pro | Lys | Thr | Pro | Glu | Glu | Val | Asn | Lys | Cys | Leu | Asp | |
| 145 | | | | | 150 | | | | | 155 | | | | | 160 | |

| gct | gtc | aac | gcc | tgt | att | aca | cag | gcc | cag | agc | tcc | att | gga | gga | gtt | 528 |
|---|---|---|---|---|---|---|---|---|---|---|---|---|---|---|---|---|
| Ala | Val | Asn | Ala | Cys | Ile | Thr | Gln | Ala | Gln | Ser | Ser | Ile | Gly | Gly | Val | |
| | | | | 165 | | | | | 170 | | | | | 175 | | |

| gtc | aac | ttt | gag | cct | tgc | gag | agc | cag | aga | gct | ctt | tgc | tat | tag | | 573 |
|---|---|---|---|---|---|---|---|---|---|---|---|---|---|---|---|---|
| Val | Asn | Phe | Glu | Pro | Cys | Glu | Ser | Gln | Arg | Ala | Leu | Cys | Tyr | | | |
| | | | 180 | | | | | 185 | | | | | 190 | | | |

<210> SEQ ID NO 9

```
<211> LENGTH: 190
<212> TYPE: PRT
<213> ORGANISM: Pseudoplectania nigrella

<400> SEQUENCE: 9

Met Lys Leu Leu Ser Leu Thr Gly Val Ala Gly Val Leu Ala Thr Cys
1               5                   10                  15

Val Ala Ala Thr Pro Leu Val Lys Cys Ala Thr Ser Gly His Tyr Gly
                20                  25                  30

Leu Ala Arg Pro Pro Arg Pro Gln Arg Ile Leu Gly Ile Leu Ser Phe
            35                  40                  45

Ser Ser Ser Gly Thr Ser Asn Asp Lys Ala Val Ala Ser Ser Ser Ile
        50                  55                  60

Ala Ala Val Asp Pro Val Thr Ser Ser Val Val Ala Ser Val Gln Val
65                  70                  75                  80

Pro Asn Phe Thr Ala Thr Asp Val Pro Thr Phe Thr Ala Thr Asp Ile
                85                  90                  95

Pro Thr Phe Thr Ala Thr Asp Val Pro Ile Phe Thr Lys Lys Pro Gln
                100                 105                 110

Gln Pro Ser Thr Leu Leu Thr Arg Thr Arg Thr His Ala Ser Val Ser
            115                 120                 125

Phe Val Ala Lys Pro Ser Ala Phe Ile Pro Lys Pro Ser Ala Ser Thr
    130                 135                 140

Ile Pro Ser Lys Pro Lys Thr Pro Glu Glu Val Asn Lys Cys Leu Asp
145                 150                 155                 160

Ala Val Asn Ala Cys Ile Thr Gln Ala Gln Ser Ser Ile Gly Gly Val
                165                 170                 175

Val Asn Phe Glu Pro Cys Glu Ser Gln Arg Ala Leu Cys Tyr
            180                 185                 190
```

CARBOHYDRATE-BINDING MODULES OF A NEW FAMILY

CROSS-REFERENCE TO RELATED APPLICATIONS

This application is a 35 U.S.C. 371 national application of PCT/DK2004/000734 filed Oct. 26, 2004, which claims priority or the benefit under 35 U.S.C. 119 of Danish application no. PA 2003 01607 filed Oct. 30, 2003 and U.S. provisional application No. 60/515,927 filed Oct. 30, 2003, the contents of which are fully incorporated herein by reference.

FIELD OF THE INVENTION

The present invention relates to non-catalytic carbohydrate-binding modules (CBM) belonging to a new family of CBM's. A CBM of the invention was found attached to a glycosyl hydrolase family 61 (GH61) polypeptide and was shown to have little homology with known CBM's indicating that it is the first known member of a new family of CBM's. The present invention further relates to CBM's preferably exhibiting binding affinity for cellulose; to a method of producing such CBM's; and to methods for using such CBM's in the textile, detergent and cellulose fiber processing industries, for purification of polypeptides, immobilisation of active enzymes, baking, manufacturing of biofuel, modification of plant cell walls.

BACKGROUND OF THE INVENTION

A carbohydrate-binding module (CBM) is defined as a contiguous amino acid sequence within a carbohydrate-active enzyme with a discrete fold having carbohydrate-binding activity. The requirement of CBM's existing as modules within larger enzymes sets this class of carbohydrate-binding protein apart from other non-catalytic sugar binding proteins such as lectins and sugar transport proteins.

CBM's were previously classified as cellulose-binding domains (CBD's) based on the initial discovery of several modules that bound cellulose (Tomme et al. (1989) FEBS Lett. 243, 239-243; Gilkes et al. (1988) J. Biol. Chem. 263, 10401-10407). However, additional modules in carbohydrate-active enzymes are continually being found that bind carbohydrates other than cellulose yet otherwise meet the CBM criteria.

Previous classification of cellulose-binding domains was based on amino acid similarity. Groupings of CBD's were called "Types" and numbered with roman numerals (e.g. Type I or Type II CBD's). In keeping with the glycoside hydrolase classification, these groupings are now called families and numbered with Arabic numerals. Families 1 to 13 are the same as Types I to XIII (Tomme et al. (1995) in Enzymatic Degradation of Insoluble Polysaccharides (Saddler & Penner eds.) 142-163, American Chemical Society, Washington).

Presently the known CBM's a reclassified in families 1-6 and 8-33. Most classified CBM's are of bacterial origin, and the known fungal carbohydrate-binding modules are mainly classified in the family CBM1. However, representatives of fungal CBM's are also found in CBM13, CBM18, CBM19, CBM20 and CBM24. Until now, only the fungal carbohydrate-binding modules from CBM1 were known to bind to crystalline cellulose. The fungal CBM's from families CBM13, CBM18, CBM19, CBM20 and CBM24 have been shown to bind to substrates such as chitin, starch and mutan. However, also the fungal carbohydrate-binding modules from CBM1 bind very well to chitin.

A number of fungal cellulases has been shown to contain a CBD of family CBM1 consisting of 36 amino acid residues. Examples of enzymes known to contain such a domain are:
Endoglucanase I (gene egl1) from *Trichoderma reesei*.
Endoglucanase II (gene egl2) from *Trichoderma reesei*.
Endoglucanase V (gene egl5) from *Trichoderma reesei*.
Exocellobiohydrolase I (gene CBHI) from *Humicola grisea, Neurospora crassa, Phanerochaete chrysosporium, Trichoderma reesei*, and *Trichoderma viride*.
Exocellobiohydrolase II (gene CBHII) from *Trichoderma reesei*.
Exocellobiohydrolase 3 (gene cel3) from *Agaricus bisporus*.
Endoglucanases B, C2, F and K from *Fusarium oxysporum*.

The CBD domain is found either at the N-terminal (Cbh-II or egl2) or at the C-terminal extremity (Cbh-I, egl1 or egl5) of these enzymes. There are four conserved cysteine residues in this type of CBD domain, all of which are involved in disulfide bonds. (Prosite, Swiss Institute of Bioinformatics).

A DNA sequence encoding a CBD from a given organism can be obtained conventionally by using PCR techniques, and, also based on current knowledge; it is possible to find homologous sequences from other organisms.

It is contemplated that new CBD's can be found by cloning cellulases, xylanases or other plant cell wall degrading enzymes and measure the binding to e.g. cellulose. If the enzyme activity is bound to Avicel® under the standard conditions described below, it can be assumed that part of the gene codes for a binding domain.

Examples of CBM-like polypeptides obtainable from plants are expansins. Expansins are not CBM's per se because they are not found encoded in the same amino acid sequence with an enzyme activity. However, it has been observed that isolated CBM domains can have expansin like activity on cellulose (Levy and Shoseyov, 2002 supra). Din et al. (Bio/Technology 9 (1991) 1096-1099) has reported that the CBD CenA from *Cellulomonas fimi* endoglucanase A is capable of nonhydrolytic disruption activity of cellulose fibers resulting in small particle release. Furthermore, it was shown that CBD CenA could prevent the flocculation of microcrystalline bacterial cellulose (Gilkes et al. (1993) Int. J. Biol. Macromol. 15:347-351). Similar phenomena were observed for other CBD's (Krull et al. (1988) Biotechnol. Bioeng. 31:321-327; Banka et al. (1998) World J. Microbiol. Biotechnol. 14:551-558; Gao et al. (2001) Acta Biochim. Biophys. Sin. 33:13-18).

CBM's are known to be used in applications as diverse as washing, treatment of textile, removal of dental plaque, purification of polypeptides, immobilisation of active enzymes, modification of cellulosic material, baking, manufacturing of biofuel, modification of plant cell walls.

SUMMARY OF THE INVENTION

The inventors have now found a carbohydrate-binding module (CBM) obtainable from the fungus *Pseudoplectania nigrella* (deposited under No. CBS 444.97) having binding affinity for cellulose, which novel CBM was found bound to an enzyme belonging to family 61 of the glycosyl hydrolases (GH61). The novel CBM (called CBMX) was shown to have affinity for Avicel® and had no observable homology (below 20%) to known CBM's. Also, none of the positions of the cysteine residues found on the CBM of the invention correspond to the positions of the well conserved cysteine residues in the family CBM1 described above. This indicates that the CBM of the invention is the first known member of a new family of CBM's.

Apart from the fungal CBM's of family CBM1 which have binding affinity for cellulose, the CBM of the invention is the first known fungal CBM shown to have binding affinity for cellulose.

The inventors have succeeded in cloning and expressing a CBM bound to a family GH61 enzyme. In addition, the inventors have expressed the domain only, without the GH61 enzyme and demonstrated that the CBM alone can bind cellulose, such as Avicel®.

Said CBM domain is encoded by the DNA sequence of positions 109-531 of SEQ ID NO:1 and has the amino acid sequence of positions 34-174 of SEQ ID NO:2. Positions 1-33 of SEQ ID NO:2 constitutes a signal peptide and an N-terminal region of the GH61 enzyme.

Accordingly, the present invention relates to a CBM of a new family of CBM's which CBM is
(a) a polypeptide encoded by the DNA sequence of positions 109-531 of SEQ ID NO:1, or a DNA sequence homologous to SEQ ID NO:1, which DNA sequence has at least 40% identity with positions 109-531 of SEQ ID NO:1, preferably at least 50% identity, more preferably at least 60% identity, more preferably at least 70% identity, more preferably at least 80%, more preferably at least 85%, more preferably at least 90%, more preferably at least 95% identity, more preferably at least 97% identity, more preferably at least 98% identity, even more preferably at least 99% identity with positions 109-531 of SEQ ID NO:1;
(b) a polypeptide produced by culturing a cell comprising the DNA sequence of positions 109-531 of SEQ ID NO:1 under conditions wherein the DNA sequence is expressed;
(c) a polypeptide having the amino acid sequence of positions 34-174 of SEQ ID NO:2, or a polypeptide homologous to SEQ ID NO:2, which polypeptide has an amino acid sequence of at least 40% identity with positions 34-174 of SEQ ID NO:2, preferably at least 50% identity, more preferably at least 60% identity, more preferably at least 70% identity, more preferably at least 80%, more preferably at least 85%, more preferably at least 90%, more preferably at least 95% identity, more preferably at least 97% identity, more preferably at least 98% identity, even more preferably at least 99% identity with positions 34-174 of SEQ ID NO:2;
(d) a polypeptide encoded by a DNA sequence that hybridizes to the DNA sequence of positions 109-531 of SEQ ID NO:1 preferably under low stringency conditions, more preferably at least under medium stringency conditions, more preferably at least under medium/high stringency conditions, more preferably at least under high stringency conditions, even more preferably at least under very high stringency conditions;
(e) a polypeptide encoded by an isolated polynucleotide molecule which polynucleotide molecule hybridizes to a denatured double-stranded DNA probe preferably under low stringency conditions, more preferably at least under medium stringency conditions, more preferably at least under medium/high stringency conditions, more preferably at least under high stringency conditions, even more preferably at least under very high stringency conditions, wherein the probe is selected from the group consisting of DNA probes comprising the sequence shown in positions 109-531 of SEQ ID NO:1, and DNA probes comprising a subsequence of positions 109-531 of SEQ ID NO:1, the subsequence having a length of at least about 100 base pairs, preferably at least 200 base pairs, more preferably at least 300 base pairs, more preferably at least 400 base pairs, more preferably at least 440 base pairs, even more preferably a length of at least 450 base pairs,
(f) a CBM polypeptide encoded by a DNA sequence obtainable from *Pseudoplectania nigrella* CBS 444.97.

In further aspects, the invention provides an expression vector comprising a DNA segment which is e.g. a polynucleotide molecule of the invention; a cell comprising the DNA segment or the expression vector; and a method of producing a CBM polypeptide, which method comprises culturing the cell under conditions permitting the production of the CBM, and recovering the CBM from the culture. Further, impurities, such as homologous impurities can be removed from the recovered CBM by use of purification methods generally known in the art.

In yet another aspect the invention provides an isolated CBM polypeptide characterized in (i) being free from homologous impurities and (ii) being produced by the method described above.

The novel CBM of the present invention is useful for washing, treatment of textile, purification of polypeptides, immobilisation of active enzymes, modification of cellulosic material, baking, manufacturing of biofuel, modification of plant cell walls.

DETAILED DESCRIPTION OF THE INVENTION

The present invention relates to non-catalytic carbohydrate-binding modules (CBM) obtainable from the fungus *Pseudoplectania nigrella* and belonging to a new family of fungal CBM's. The CBM of the invention was found in association with a protein belonging to family 61 of the glycosyl hydrolases. The CBM of the invention is encoded by the DNA sequence of positions 109-531 of SEQ ID NO:1 and has the amino acid sequence of positions 34-174 of SEQ ID NO:2. Said CBM preferably exhibits binding affinity for cellulose. The present invention relates to a method of producing such CBM's; and to methods for using such CBM's in washing applications, for treatment of textile, purification of polypeptides, immobilisation of active enzymes, modification of cellulosic material, baking, manufacturing of biofuel, modification of plant cell walls.

The inventors have succeeded in cloning and expressing a CBM bound to a family GH61 enzyme. In addition, the inventors have expressed the domain only, without the GH61 enzyme and demonstrated that the CBM alone can bind cellulose. Accordingly, the invention relates to a CBM of a new family of CBM's which CBM is
(a) a polypeptide encoded by the DNA sequence of positions 109-531 of SEQ ID NO:1, or a DNA sequence homologous to SEQ ID NO:1, which DNA sequence has at least 40% identity with positions 109-531 of SEQ ID NO:1, preferably at least 50% identity, more preferably at least 60% identity, more preferably at least 70% identity, more preferably at least 80%, more preferably at least 85%, more preferably at least 90%, more preferably at least 95% identity, more preferably at least 97% identity, more preferably at least 98% identity, even more preferably at least 99% identity with positions 109-531 of SEQ ID NO:1;
(b) a polypeptide produced by culturing a cell comprising the DNA sequence of positions 109-531 of SEQ ID NO:1 under conditions wherein the DNA sequence is expressed;
(c) a polypeptide having the amino acid sequence of positions 34-174 of SEQ ID NO:2, or a polypeptide homologous to SEQ ID NO:2, which polypeptide has an amino acid sequence of at least 40% identity with positions 34-174 of SEQ ID NO:2, preferably at least 50% identity, more preferably at least 60% identity, more preferably at least 70% identity, more preferably at least 80%, more preferably at least 85%, more preferably at least 90%, more preferably at least 95% identity, more preferably at least 97% identity, more preferably at least 98% identity, even more preferably at least 99% identity with positions 34-174 of SEQ ID NO:2;

(d) a polypeptide encoded by a DNA sequence that hybridizes to the DNA sequence of positions 109-531 of SEQ ID NO:1 preferably under low stringency conditions, more preferably at least under medium stringency conditions, more preferably at least under medium/high stringency conditions, more preferably at least under high stringency conditions, even more preferably at least under very high stringency conditions;

(e) a polypeptide encoded by an isolated polynucleotide molecule which polynucleotide molecule hybridizes to a denatured double-stranded DNA probe preferably under low stringency conditions, more preferably at least under medium stringency conditions, more preferably at least under medium/high stringency conditions, more preferably at least under high stringency conditions, even more preferably at least under very high stringency conditions, wherein the probe is selected from the group consisting of DNA probes comprising the sequence shown in positions 109-531 of SEQ ID NO:1, and DNA probes comprising a subsequence of positions 109-531 of SEQ ID NO:1, the subsequence having a length of at least about 100 base pairs, preferably at least 200 base pairs, more preferably at least 300 base pairs, more preferably at least 400 base pairs, more preferably at least 440 base pairs, even more preferably a length of at least 450 base pairs, (f) a CBM polypeptide encoded by a DNA sequence obtainable from *Pseudoplectania nigrella* CBS 444.97.

Hybridization

Suitable experimental conditions for determining hybridization at low to very high stringency between a nucleotide probe and a homologous DNA or RNA sequence involves presoaking of the filter containing the DNA fragments or RNA to hybridize in 5×SSC (Sodium chloride/Sodium citrate as described in Sambrook et al. (1989) Molecular Cloning: A Laboratory Manual, Cold Spring Harbor Lab., Cold Spring Harbor, N.Y.) for 10 min, and prehybridization of the filter in a solution of 5×SSC, 5×Denhardt's solution (Sambrook et al. 1989 supra), 0.5% SDS and 100 µg/ml of denatured sonicated salmon sperm DNA (Sambrook et al. 1989 supra), followed by hybridization in the same solution containing a concentration of 10 ng/ml of a random-primed (Feinberg and Vogelstein (1983) Anal. Biochem. 132, 6-13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Sequence Alignment and Identity

Nucleotide sequences may be aligned with the AlignX application of the Vector NTI Program Suite 7.0 (Informax, a subsidiary of Invitrogen Inc.) using the default settings, which employ a modified ClustalW algorithm (Thompson et al. (1994) Nuc. Acid Res. 22:4673-4680), the swgapdnamt score matrix, a gap opening penalty of 15 and a gap extension penalty of 6.66.

Amino acid sequences may be aligned with the AlignX application of the Vector NTI Program Suite v8 (Informax, a subsidiary of Invitrogen Inc) using default settings, which employ a modified ClustalW algorithm (Thompson, et al. (1994) supra), the blosum62mt2 score matrix, a gap opening penalty of 10 and a gap extension penalty of 0.1.

In a Smith-Waterman search (Smith and Waterman (1981) J. Mol. Biol. 147:195-197), generally considered to be very sensitive, two proteins registered some similarity at the amino acid level. The first was FIG. 2 of *Saccharomyces cerevisiae* (Swiss-Prot No. p25653). The Smith-Waterman score was 162, and showed 28.7% identity over a 143 base pair overlap. Explanation of homology: Both the CBM of the invention and FIG. 2 are highly serine-threonine rich. The region of similarity between the two proteins is thought to be highly glycosylated in FIG. 2. It could be that the pattern similarities in this region have more to do with glycosylation recognition than actual functional similarities. The second protein showing some similarity was a hypothetical protein from *Arthrobacter nicotinovorans* (SPTREMBL:Q8GAM3). The protein has a Smith-Waterman score of 138 and was 30.5% identical in a 128 amino acid overlap. Homology is rather low overall. It is doubtful that these two proteins are either evolutionarily or functionally related.

Size and 3D Structure

The CBM of the invention has six phenylalanine repeats at a spacing that would potentially put them on the same surface of a higher order structure such as a beta barrel or alpha helix. The three dimensional structures of representative members of CBM families 1-6, 9 and 15 have been resolved by x-ray crystallography and NMR and according to Levy and Shoseyov (Biotechnology Advances 20 (2002) 191-213), data from these structures indicate that CBD's from different families are structurally similar and that their cellulose binding capacity can be attributed, at least in part, to several aromatic amino acids that compose their hydrophobic surface. The present inventors therefore wish to point out several phenylalanine residues and their significance to the ability of the CBM of the invention to bind cellulose. Below are sub-regions of the CBM with the residues marked: VPNFTATDVPTFTATDIPTFTATDVPIFTKKPQQPS (positions 64-99 of SEQ ID NO:2), and farther towards the C-terminus SVSFVAKPSAFIPKPSA (positions 110-126 of SEQ ID NO:2).

The expressed CBM or CBM-containing polypeptide of the invention has a molecular weight (Mw) which is equal to or higher than about 15 kD in an unglycosylated form. The majority of the protein binding to Avicel® appeared as a broad band of molecular weight 35-45 kDa, which is considerably higher than the 15 kDa of the protein part of the carbohydrate binding module. The high and heterogeneous molecular weight is probably due to heterogeneity in O- and N-glycosylation of the N-terminal part of the protein. For heterologously expressed CBMX in *Aspergillus oryzae* the size of CBMX can vary from 14 kDa to almost 70 kDa due to heterologous glycosylation of the protein. Moreover, N-terminal sequencing of the 35-45 kDa band gave exclusively the sequence SFSSSGT (positions 47-53 of SEQ ID NO:9) indicating that heterogeneity in the N-terminal amino acid sequence is not present.

Preferably, the molecular weight of the CBM of the invention in an unglycosylated form is equal to or below about 70 kD, more preferably equal to or below 50 kD, more preferably equal to or below about 40 kD or 30 kD, even more preferably equal to or below about 25 kD, even more preferably equal to or below about 20 kD, even more preferably equal to or below about 15 kD.

Carbohydrate-Binding Modules

Although a number of types of carbohydrate-binding modules have been described in the patent and scientific literature, the majority thereof, many of which derive from cellulolytic enzymes, are commonly referred to as cellulose-binding domains (CBD); a typical CBM will thus be one which occurs in a cellulase and which binds preferentially to cellulose and/or to poly- or oligosaccharide fragments thereof.

Cellulose-binding (and other carbohydrate-binding) modules are polypeptide amino acid sequences which occur as integral parts of large polypeptides or proteins consisting of two or more polypeptide amino acid sequence regions, especially in hydrolytic enzymes (hydrolases) which typically comprise a catalytic domain containing the active site for substrate hydrolysis and a carbohydrate-binding domain for binding to the carbohydrate substrate in question. Such enzymes can comprise more than one catalytic domain and one, two or three carbohydrate-binding domains, and they may further comprise one or more polypeptide amino acid sequence regions linking the carbohydrate-binding domain(s) with the catalytic domain(s), a region of the latter type usually being denoted a "linker".

In the protein complex, typically a hydrolytic enzyme, a CBM is located either at the N or C terminal or is internal. A monomeric CBM typically consists of more than about 30 and less than about 250 amino acid residues. For example, a CBM classified in Family I consists of 33-37 amino acid residues; a CBM classified in Family IIa consists of 95-108 amino acid residues; and a CBM classified in Family VI consists of 85-92 amino acid residues. Accordingly, the molecular weight of a monomeric CBM will typically be in the range of from about 4 kD to about 40 kD, and usually below about 35 kD. CBM's may be useful as a single domain polypeptide or as a dimer, a trimer, or a polymer; or as a part of a protein hybrid.

Examples of hydrolytic enzymes comprising a carbohydrate-binding module are cellulases, xylanases, mannanases, arabinofuranosidases, acetylesterases, amylases, glucoamylases, mutanases and chitinases. CBM's have been shown to bind to carbohydrates such as cellulose, xylan, starch, chitin, mannan, beta-glucans, mutan and cyclodextrins. CBM's have been found in plants and algae, e.g. in the red alga *Porphyra purpurea* in the form of a non-hydrolytic polysaccharide-binding protein (see Tomme et al. (1996) Cellulose-Binding Domains, Classification and Properties in Enzymatic Degradation of Insoluble Carbohydrates, Saddler & Penner (Eds.), ACS Symposium Series, No. 618).

Washing

The present invention thus relates, inter alia, to a process for removal or bleaching of soiling or stains present on cellulosic fabric or textile, wherein the fabric or textile is contacted in aqueous medium with a modified enzyme (enzyme hybrid) which comprises a catalytically (enzymatically) active amino acid sequence of a non-cellulolytic enzyme linked to an amino acid sequence comprising a carbohydrate-binding module, such as a CBD.

Stains

Soiling or stains which may be removed according to the present invention include those already mentioned above, i.e. soiling or stains originating from, for example, starch, proteins, fats, red wine, fruit (such as blackcurrant, cherry, strawberry or tomato, in particular tomato in ketchup or spaghetti sauce), vegetables (such as carrot or beetroot), tea, coffee, spices (such as curry or paprika), body fluids, grass, or ink (e.g. from ball-point pens or fountain pens). Other types of soiling or stains which are appropriate targets for removal or bleaching in accordance with the invention include sebum, soil (i.e. earth), clay, oil and paint. A process for removal or bleaching of soiling or stains present on cellulosic fabric is described in WO 97/28243. The process comprises contacting a fabric with an aqueous medium comprising a modified enzyme, which enzyme is a catalytically active amino acid sequence of a non-cellulolytic enzyme which is linked to an amino acid sequence comprising a cellulose-binding domain.

It is an object of the present invention to use the CBM of SEQ ID NO:2 in a process for removal or bleaching of soiling or stains present on cellulosic fabric as described in WO 97/28243.

Cellulosic Fabric

The term "cellulosic fabric" is intended to indicate any type of fabric, in particular woven fabric, prepared from a cellulose-containing material, such as cotton, or from a cellulose-derived material (prepared, e.g., from wood pulp or from cotton).

In the present context, the term "fabric" is intended to include garments and other types of processed fabrics, and is used interchangeably with the term "textile".

Examples of cellulosic fabric manufactured from naturally occurring cellulosic fibre are cotton, ramie, jute and flax (linen) fabrics. Examples of cellulosic fabrics made from man-made cellulosic fibre are viscose (rayon) and lyocell (e.g. Tencel™) fabric; also of relevance in the context of the invention are all blends of cellulosic fibres (such as viscose, lyocell, cotton, ramie, jute or flax) with other fibres, e.g. with animal hair fibres such as wool, alpaca or camel hair, or with polymer fibres such as polyester, polyacrylic, polyamide or polyacetate fibres.

Specific examples of blended cellulosic fabric are viscose/cotton blends, lyocell/cotton blends (e.g. Tencel™/cotton blends), viscose/wool blends, lyocell/wool blends, cotton/wool blends, cotton/polyester blends, viscose/cotton/polyester blends, wool/cotton/polyester blends, and flax/cotton blends.

Enzyme Hybrids

Enzyme classification numbers (EC numbers) referred to in the present patent application are in accordance with the Recommendations (1992) of the Nomenclature Committee of the International Union of Biochemistry and Molecular Biology, Academic Press Inc., 1992.

A modified enzyme (enzyme hybrid) for use in accordance with the invention comprises an enzymatically active amino acid sequence of a non-cellulolytic enzyme (i.e. a catalytically active amino acid sequence of an enzyme other than a cellulase) useful in relation to the cleaning of fabric or textile, typically the removal or bleaching of soiling or stains from fabrics or textiles in washing processes. Preferred are enzymes selected from the group consisting of amylases (e.g. α-amylases, EC 3.2.1.1), proteases (i.e. peptidases, EC 3.4), lipases (e.g. triacylglycerol lipases, EC 3.1.1.3) and oxidoreductases (e.g. peroxidases, EC 1.11.1, such as those classified under EC 1.11.1.7; or phenol-oxidizing oxidases, such as laccases, EC 1.10.3.2, or other enzymes classified under EC 1.10.3), fused (linked) to an amino acid sequence comprising a cellulose-binding module. The catalytically active amino acid sequence in question may comprise or consist of the whole, or substantially the whole of the full amino acid sequence of the mature enzyme in question, or it may consist of a portion of the full sequence which retains substantially the same enzymatic properties as the full sequence.

Modified enzymes of the type in question, as well as detailed descriptions of the preparation and purification thereof, are known in the art (see, e.g., WO 90/00609, WO 94/24158 and WO 95/16782). They may be prepared by transforming into a host cell a DNA construct comprising at least a fragment of DNA encoding the CBM ligated, with or without a linker, to a DNA sequence encoding the enzyme of interest, and growing the transformed host cell to express the fused gene. One relevant, but non-limiting, type of recombinant product (enzyme hybrid) obtainable in this manner, often referred to in the art as a "fusion protein", may be described by one of the following general formulae:

A-CBM-MR-X-B

A-X-MR-CBM-B

In the latter formulae, CBM is an amino acid sequence comprising at least the carbohydrate-binding module (CBM) per se.

MR (the middle region; a linker) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker.

X is an amino acid sequence comprising the above-mentioned, enzymatically active sequence of amino acid residues of a polypeptide encoded by a DNA sequence encoding the non-cellulolytic enzyme of interest.

The moieties A and B are independently optional. When present, a moiety A or B constitutes a terminal extension of a CBM or X moiety, and normally comprises one or more amino acid residues.

It will thus, inter alia, be apparent from the above that a CBM in an enzyme hybrid of the type in question may be positioned C-terminally, N-terminally or internally in the enzyme hybrid. Correspondingly, an X moiety in an enzyme hybrid of the type in question may be positioned N-terminally, C-terminally or internally in the enzyme hybrid.

Enzyme hybrids of interest in the context of the invention include enzyme hybrids which comprise more than one CBM, e.g. such that two or more CBM's are linked directly to each other, or are separated from one another by means of spacer or linker sequences, consisting typically of a sequence of amino acid residues of appropriate length. Two CBM's in an enzyme hybrid of the type in question may, for example, also be separated from one another by means of an -MR-X- moiety as defined above.

A very important issue in the construction of enzyme hybrids of the type in question is the stability towards proteolytic degradation. Two- and multi-domain proteins are particularly susceptible towards proteolytic cleavage of linker regions connecting the domains. Proteases causing such cleavage may, for example, be subtilisins, which are known to often exhibit broad substrate specificities (see, e.g.: Grøn et al. (1992) Biochemistry 31:6011-6018; Teplyakov et al. (1992) Protein Engineering 5:413-420).

Glycosylation of linker residues in eukaryotes is one of Nature's ways of preventing proteolytic degradation. Another is to employ amino acids which are less favoured by the surrounding proteases. The length of the linker also plays a role in relation to accessibility by proteases. Which "solution" is optimal depends on the environment in which the enzyme hybrid is to function. When constructing new enzyme hybrid molecules, linker stability thus becomes an issue of great importance.

Cellulases (Cellulase Genes) Useful for Preparation of CBM's

Techniques suitable for isolating a cellulase gene are well known in the art. In the present context, the terms "cellulase" and "cellulolytic enzyme" refer to an enzyme which catalyses the degradation of cellulose to glucose, cellobiose, triose and/or other cello-oligosaccharides.

Preferred cellulases (i.e. cellulases comprising preferred CBM's) in the present context are microbial cellulases, particularly bacterial or fungal cellulases. Endoglucanases, notably endo-1,4-β-glucanases (EC 3.2.1.4), particularly monocomponent (recombinant) endo-1,4β-glucanases, are a preferred class of cellulases.

Useful examples of bacterial cellulases are cellulases derived from or producible by bacteria from the group consisting of *Pseudomonas, Bacillus, Cellulomonas, Clostridium, Microspora, Thermotoga, Caldocellum* and Actinomycetes such as *Streptomyces, Termomonospora* and *Acidothemus*, in particular from the group consisting of *Pseudomonas cellulolyticus, Bacillus lautus, Cellulomonas fimi, Clostridium thermocellum, Microspora bispora, Termomonospora fusca, Termomonospora cellulolyticum* and *Acidothemus cellulolyticus*.

The cellulase may be an acid, a neutral or an alkaline cellulase, i.e. exhibiting maximum cellulolytic activity in the acid, neutral or alkaline range, respectively.

A useful cellulase is an acid cellulase, preferably a fungal acid cellulase, which is derived from or producible by fungi from the group of genera consisting of *Trichoderma, Myrothecium, Aspergillus, Phanaerochaete, Neurospora, Neocallimastix* and *Botrytis*.

A preferred useful acid cellulase is one derived from or producible by fungi from the group of species consisting of *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum, Pseudoplectania nigrella* and *Botrytis cinerea*.

Another useful cellulase is a neutral or alkaline cellulase, preferably a fungal neutral or alkaline cellulase, which is derived from or producible by fungi from the group of genera consisting of *Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium, Pseudoplectania nigrella* and *Acremonium*.

A preferred alkaline cellulase is one derived from or producible by fungi from the group of species consisting of *Humicola insolens, Fusarium oxysporum, Myceliopthora thermophila, Penicillium janthinellum* and *Cephalosporium* sp., preferably from the group of species consisting of *Humicola insolens* DSM 1800, *Fusarium oxysporum* μM 2672, *Myceliopthora thermophila* CBS 117.65, and *Cephalosporium* sp. RYM-202.

Other examples of useful cellulases are variants of parent cellulases of fungal or bacterial origin, e.g. variants of a parent cellulase derivable from a strain of a species within one of the fungal genera *Humicola, Trichoderma* or *Fusarium*.

Amylolytic Enzymes

Amylases (e.g. α- or β-amylases) which are appropriate as the basis for enzyme hybrids of the types employed in the context of the present invention include those of bacterial or fungal origin. Chemically or genetically modified mutants of such amylases are included in this connection. Relevant α-amylases include, for example, α-amylases obtainable from *Bacillus* species, in particular a special strain of *B. licheniformis*, described in more detail in GB 1296839. Relevant commercially available amylases include Duramyl®, Termamyl®, Fungamyl® and BAN® (all available from Novozymes A/S, Bagsvaerd, Denmark), and Rapidase™ and Maxamyl™ P (available from DSM, Holland).

Other useful a mylolytic enzymes are C GTases (cyclodextrin glucanotransferases, E C 2.4.1.19), e.g. those obtainable from species of *Bacillus, Thermoanaerobactor* or *Thermoanaerobacterium*.

Proteolytic Enzymes

Proteases (peptidases) which are appropriate as the basis for enzyme hybrids of the types employed in the context of the present invention include those of animal, vegetable or microbial origin. Proteases of microbial origin are preferred. Chemically or genetically modified mutants of such proteases are included in this connection. The protease may be a serine protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270.

Relevant commercially available protease enzymes include Alcalase®, Savinase® and Esperase® (all available from Novozymes A/S, Bagsvaerd, Denmark), Maxatase™, Maxacal™, Maxapem™ and Properase™ (available from DSM, Holland), Purafect™ and Purafect™ OXP (available from Genencor International, USA), and Opticlean™ and Optimase™ (available from by Solvay Enzymes).

Lipolytic Enzymes

Lipolytic enzymes (lipases) which are appropriate as the basis for enzyme hybrids of the types employed in the context of the present invention include those of bacterial or fungal origin. Chemically or genetically modified mutants of such lipases are included in this connection.

Examples of useful lipases include a *Humicola lanuginosa* lipase, e.g. as described in EP 258 068 and EP 305 216; a *Rhizomucor miehei* lipase, e.g. as described in EP 238 023; a *Candida* lipase, such as a *C. antarctica* lipase, e.g. the *C. antarctica* lipase A or B described in EP 214 761; a *Pseudomonas lipase*, such as one of those described in EP 721 981 (e.g. a lipase obtainable from a *Pseudomonas* sp. SD705 strain having deposit accession number FERM BP-4772), in PCT/JP96/00426, in PCT/JP96/00454 (e.g. a *P. solanacearum* lipase), in EP 571 982 or in WO 95/14783 (e.g. a *P. mendocina* lipase), a *P. alcaligenes* or *P. pseudoalcaligenes* lipase, e.g. as described in EP 218 272, a *P. cepacia* lipase, e.g. as described in EP 331 376, a *P. stutzeri* lipase, e.g. as disclosed in GB 1,372,034, or a *P. fluorescens* lipase; a *Bacillus* lipase, e.g. a *B. subtilis* lipase (Dartois et al. (1993) Biochemica et Biophysica Acta 1131:253-260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al. (1991) in Gene 103:61-67, the *Geotricum candidum* lipase (Schimada et al. (1989) J. Biochem. 106: 383-388), and various *Rhizopus* lipases such as an *R. delemar* lipase (Hass et al. (1991) Gene 109:117-113), an *R. niveus* lipase (Kugimiya et al. (1992) Biosci. Biotech. Biochem. 56:716-719) and a *R. oryzae* lipase.

Other potentially useful types of lipolytic enzymes include cutinases, e.g. a cutinase derived from *Pseudomonas mendocina* as described in WO 88/09367, or a cutinase derived from *Fusarium solani* f. *pisi* (described, e.g., in WO 90/09446).

Suitable commercially available lipases include Lipolase® and Lipolase Ultra® (available from Novozymes A/S), M1 Lipase™, Lumafast™ and Lipomax™ (available from DSM, Holland) and Lipase P "Amano" (available from Amano Pharmaceutical Co. Ltd.).

Oxidoreductases

Oxidoreductases which are appropriate as the basis for enzyme hybrids of the types employed in the context of the present invention include peroxidases (EC 1.11.1) and oxidases, such as laccases (EC 1.10.3.2) and certain related enzymes.

Peroxidases

Peroxidases (EC 1.11.1) are enzymes acting on a peroxide (e.g. hydrogen peroxide) as acceptor. Very suitable peroxidases are those classified under EC 1.11.1.7, or any fragment derived therefrom, exhibiting peroxidase activity. Synthetic or semisynthetic derivatives thereof (e.g. with porphyrin ring systems, or microperoxidases, cf., for example, U.S. Pat. No. 4,077,768, EP 537 381, WO 91/05858 and WO 92/16634) may also be of value in the context of the invention.

Very suitable peroxidases are peroxidases obtainable from plants (e.g. horseradish peroxidase or soy bean peroxidase) or from microorganisms, such as fungi or bacteria. In this respect, some preferred fungi include strains belonging to the subdivision Deuteromycotina, class Hyphomycetes, e.g. *Fusarium, Humicola, Tricoderma, Myrothecium, Verticillum, Arthromyces, Caldariomyces, Ulocladium, Embellisia, Cladosporium* or *Dreschlera*, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g. *Coprinus, Phanerochaete, Coriolus* or *Trametes*, in particular *Coprinus cinereus* f. *microsporus* (IFO 8371), *Coprinus macrorhizus, Phanerochaete chrysosporium* (e.g. NA-12) or *Trametes versicolor* (e.g. PR4 28-A).

Further preferred fungi include strains belonging to the subdivision Zygomycotina, class Mycoraceae, e.g. *Rhizopus* or *Mucor*, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp; *verticillium*.

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to *Myxococcus*, e.g. *M. virescens*.

Other potential sources of useful particular peroxidases are listed in Saunders et al. (1964) Peroxidase, 41-43 London.

The peroxidase may furthermore be one which is producible by a method comprising cultivating a host cell—transformed with a recombinant DNA vector which carries a DNA sequence encoding said peroxidase as well as DNA sequences encoding functions permitting the expression of the DNA sequence encoding the peroxidase—in a culture medium under conditions permitting the expression of the peroxidase, and recovering the peroxidase from the culture.

A suitable recombinantly produced peroxidase is a peroxidase derived from a *Coprinus* sp., in particular *C. macrorhizus* or *C. cinereus* according to WO 92/16634, or a variant thereof, e.g. a variant as described in WO 94/12621.

Oxidases and Related Enzymes

Preferred oxidases in the context of the present invention are oxidases classified under EC 1.10.3, which are oxidases employing molecular oxygen as acceptor (i.e. enzymes catalyzing oxidation reactions in which molecular oxygen functions as oxidizing agent).

As indicated above, laccases (EC 1.10.3.2) are very suitable oxidases in the context of the invention. Examples of other useful oxidases in the context of the invention include the catechol oxidases (EC 1.10.3.1) and bilirubin oxidases (EC 1.3.3.5). Further useful, related enzymes include monophenol monooxygenases (EC 1.14.18.1).

Laccases are obtainable from a variety of plant and microbial sources, notably from bacteria and fungi (including filamentous fungi and yeasts), and suitable examples of laccases are to found among those obtainable from fungi, including laccases obtainable from strains of *Aspergillus, Neurospora* (e.g. *N. crassa*), *Podospora, Botrytis, Collybia, Fomes, Lentinus, Pleurotus, Trametes* (e.g. *T. villosa* or *T. versicolor* [some species/strains of *Trametes* being known by various names and/or having previously been classified within other genera; e.g. *Trametes villosa=T. pinsitus=Polyporus pinsitis* (also known as *P. pinsitus* or *P. villosus*)=*Coriolus pinsitus*], *Polyporus, Rhizoctonia* (e.g. *R. solani*), *Coprinus* (e.g. *C. plicatilis* or *C. cinereus*), *Psatyrella, Myceliophthora* (e.g. *M. thermophila*), *Schytalidium, Phlebia* (e.g. *P. radita*; see WO 92/01046), *Coriolus* (e.g. *C. hirsutus*; see JP 2-238885), *Pyricularia* or *Rigidoporus*.

Preferred laccases in the context of the invention include laccase obtainable from species/strains of *Trametes* (e.g. *T. villosa*), *Myceliophthora* (e.g. *M. thermophila*), *Schytalidium* or *Polyporus*.

Other Enzymes

Further classes of enzymes which are appropriate as the basis for enzyme hybrids of the types employed in the context of the present invention include pectinases such as pectate lyase (EC 4.2.2.2), pectin lyase (EC 4.2.2.10), rhamnogalacturonan lyase (EC not defined), endo-1,4-galactanase (EC 3.2.1.89), xyloglucanase (EC not defined), xylanase (EC 3.2.1.8), arabinanase (EC 3.2.1.99), alpha-L-arabinofuranosidase (EC 3.2.1.55), Mannan endo-1,4-mannosidase (EC 3.2.1.78), beta-mannosidase (EC 3.2.1.25), beta-1,3-1,4-glucanase (EC 3.2.1.73), rhamnogalacturonan hydrolase, exopolygalacturonase (EC 3.2.1.67), rhamnogalacturonase (EC not defined), Cellulase (EC 3.2.1.4), Glucan 1,3-beta-glucosidase (EC 3.2.1.58), Licheninase (EC 3.2.1.73), Glucan endo-1,6-beta-glucosidase (EC 3.2.1.75), Mannan endo-1,4-beta-mannosidase (EC 3.2.1.78), Endo-1,4-beta-xylanase (EC 3.2.1.8), Cellulose 1,4-cellobiosidase (EC 3.2.1.91), cellobiohydrolase (EC 3.2.1.91). (polygalacturonases (EC 3.2.1.15). Acetyl and methyl esterase enzymes such as: rhamnogalacturonan methyl esterase, rhamnogalacturonan acetyl esterase, pectin methylesterase (EC 3.1.1.1.11), pectin acetylesterase (EC not defined), xylan methyl esterase, acetyl xylan esterase (EC 3.1.1.72), feruloyl esterase (EC 3.1.1.73), cinnamoyl esterase (EC 3.1.1.73).

Detergents

The CBM of the invention may be added to a detergent for washing textile, such as a laundry detergent or a detergent for washing hard surfaces, such as a dish washing detergent. A detergent composition comprising the CBM of the invention can further comprise one or more enzymes selected from the group consisting of proteases, cellulases (endo-glucanases), beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; or mixtures thereof.

Further, a detergent composition in accordance with the invention may contain ordinary detergent components such as for example a surfactant, a builder, a bleach, a suds suppressor as described in WO 99/27082.

Treatment of Textile

During the weaving of textiles, the threads are exposed to considerable mechanical strain. In order to prevent breaking, they are usually reinforced by coating (sizing) with a gelatinous substance called "size".

The most common sizing agent is starch in native or modified form. However, other polymeric substances, for example poly-vinylalcohol (PVA), polyvinylpyrrolidone (PVP), polyacrylic acid (PAA) or derivatives of cellulose [e.g. carboxymethylcellulose (CMC), hydroxyethylcellulose, hydroxypropyl-cellulose or methylcellulose] may also be abundant in the size. Small amounts of, e.g., fats or oils may also be added to the size as a lubricant.

As a consequence of the presence of the size, the threads of the fabric are not able to absorb water, finishing agents or other compositions (e.g. bleaching, dyeing or crease-proofing compositions) to a sufficient degree. Uniform and durable finishing of the fabric can thus be achieved only after removal of the size from the fabric; a process of removing size for this purpose is known as a "desizing" process.

In cases where the size comprises a starch, the desizing treatment may be carried out using a starch-degrading enzyme (e.g. an amylase). In cases where the size comprises fat and/or oil, the desizing treatment may comprise the use of a lipolytic enzyme (a lipase). In cases where the size comprises a significant amount of carboxymethylcellulose (CMC) or other cellulose-derivatives, the desizing treatment may be carried out with a cellulolytic enzyme, either alone or in combination with other substances, optionally in combination with other enzymes, such as amylases and/or lipases.

It is an object of the present invention to achieve improved enzyme performance under desizing conditions by modifying the enzyme so as to alter (increase) the affinity of the enzyme for cellulosic fabric, whereby the modified enzyme comes into closer contact with the sizing agent in question.

The present invention thus relates, inter alia, to a process for desizing cellulosic fabric or textile, wherein the fabric or textile is treated (normally contacted in aqueous medium) with a modified enzyme (enzyme hybrid) which comprises a catalytically (enzymatically) active amino acid sequence of an enzyme, in particular of a non-cellulolytic enzyme, linked to an amino acid sequence comprising a carbohydrate-binding module, such as the CBM of SEQ ID NO:2. This process is described in further detail in WO 97/28256.

The term "desizing" is intended to be understood in a conventional manner, i.e. the removal of a sizing agent from the fabric.

Scouring

The scouring process removes non-cellulosic material from the cotton fiber, especially the cuticle (mainly consisting of waxes) and primary cell wall (mainly consisting of pectin, protein and xyloglucan) before bleaching and dying of the textile. A proper wax removal is necessary for obtaining a high wettability, being a measure for obtaining a good dyeing. Removal of the primary cell wall improves wax removal and ensures a more even dyeing. Further this improves the whiteness in the bleaching process.

The CBM's of family CBM1 are known to wedge into crystalline cellulose like expansins and swollenins, and aid in the release of non cellulose components or contaminants from textile. The dye accessibility can be increased by treating the textile with CBM's. The CBM's of the invention have properties similar to the CBM's of family CBM1. Accordingly, the CBM's of the invention may be used to remove non-cellulosic material from the cotton fiber in the scouring process.

Affinity Tags

CBM's that bind reversibly to carbohydrates are useful for separation and purification of target polypeptides. CBM's of family I bind reversibly to crystalline cellulose and are useful tags for affinity chromatography.

It is an object of the present invention to achieve improved separation and purification of target polypeptides by use of CBM's as affinity tags as describes by Terpe (2003) Appl. Microbiol. Biotechnol. 60:523-533 and U.S. Pat. No. 5,670, 623.

Immobilisation of Molecules

Some CBM's bind irreversibly to cellulose and can be used for immobilization of molecules such as metallothioneins, phytochelatins or enzymes. Such an immobilization is useful in e.g. removal of heavy metal contaminations from the environment, wherein the heavy metal ions bind to polypeptides biosorbents such as metallothioneins or phytochelatins, and the CBM-biosorbent-heavy metal complex is irreversibly immobilized by the binding of the CBM to a carbohydrate material (Xu et al. (2002) Biomacromolecules 3:462-465. It is an object of the present invention to achieve immobilization of molecules such as metallothioneins, phytochelatins or enzymes by use of the CBM of SEQ ID NO:2 as fusion proteins. Further, a method for removal contaminants such as heavy metals from the environment, by immobilization with CBM's it is an object of the present invention.

CBM Conjugates

A carbohydrate-binding domain conjugate, such as a CBD conjugate, comprises at least two CBD's attached to a polysaccharide. The polysaccharide may be capable of binding to cellulose, and is conveniently locust bean gum. CBD conjugates are able to increase the strength of cellulosic material such as fabric by cross-linking fibres as described in GB 2376017 to Unilever. It is an object of the present invention to increase the strength and wear of the fabric by cross-linking fibres by use of the CBM of SEQ ID NO:2.

The CBD conjugates may also be used as delivery vehicles to deposit materials on textile in any stage of the laundering process. This latter application can be achieved by coating the benefit agent, either directly by chemical means or indirectly via a compound associated with the benefit agent e.g. a capsule as described in GB 2376017 to Unilever. Examples of such benefit agents are softening agents, finishing agents, protecting agents, fragrances such as perfumes and bleaching agents.

Examples of softening agents are clays, cationic surfactants or silicon compounds. Examples of finishing agents and protecting agents are polymeric lubricants, soil repelling agents, soil release agents, photo-protective agents such as sunscreens, anti-static agents, dye-fixing agents, anti-bacterial agents and anti-fungal agents. The fragrances or perfumes may be encapsulated, e.g. in latex or microcapsules or gelatin based coacervates. It is an object of the present invention to use of the CBM of SEQ ID NO:2 as a delivery vehicle to deposit materials on textile in the laundry process.

Baking

It is known that adding CBM's to xylanases or amylases or other baking active enzymes, may result in better performance in baking trials than enzymes without CBM's. In WO 98/16112 it is described how antistaling enzymes such as amylolytic enzymes was fused to a CBD and used to retard staling and aging of baked bread. It is an object of the present invention to fuse the CBM of SEQ ID NO:2 with amylolytic enzymes and use it to retard staling and aging of baked bread as described in WO 98/16112.

Use of CBM's for Production of Bioethanol

Ethanol can be produced from agricultural waste or biomass (biofuel). The ethanol convertible components of many types of biomass (for example, corn stover, wood pulp and wheat straw) consists largely of crystalline cellulose. Crystalline cellulose is naturally resistant to enzymatic degradation because the cellulose fibrils are tightly packed together thus creating an accessibility problem for cellulose degrading enzymes. A number of methods for opening the structure of crystalline cellulose in biomass are being investigated: acid pre-treatment with steam explosion is one well studied method (Bura et al. (2002) Appl Biochem Biotechnol. 98-100:59-72). Wet oxidation is another method described by Naito et al. (2001) Journal of Chemical Engineering of Japan, 34(12) 1545-1548.

There is clear evidence that cellulose binding domains alone can alter the characteristics of crystalline cellulose (Shoseyov et al. (2002) Proceedings of the 223th American Chemical Society National Meeting. Orlando, Fla., USA. It is an object of the present invention to use the CBM of the invention for disruption of the microcrystalline nature of the cellulose microfibrils found in biomass for production of biofuel so as to increase accessibility of cellulose degrading enzymes to the biomass.

Modification of Plant Cell Walls

By introducing a gene encoding a CBM such as a CBD into plants or microorganisms it is possible to express CBD proteins within the cell wall of the microorganism or plant tissue. CBD proteins have been shown to bind to newly synthesized cellulose fibres in plant cell walls, and this physico-mechanical interference uncouples cellulose synthesis by the subunits of the cellulose synthase enzyme complexes. This results in an increased rate of synthesis of the cellulose polymer, improved polymer qualities and enhanced biomass. The increased rate of cellulose synthesis in the cell wall leads to enhanced cellulose production, greater biomass at the plant level, improved fibre properties and may enhance resistance to biotic and abiotic stress. A CBD encoding gene can be inserted into hardwood forestry species and subsequent substantial volume increases with improvements in wood density and fibre properties can be demonstrated. These improvements will carry through to the finished paper, exhibiting enhanced tensile, tear and burst indices (U.S. Pat. No. 6,184, 440).

It is an object of the present invention to insert the CBM encoding DNA sequence of SEQ ID NO:1 into a plant in order to alter the cell walls of said plant, resulting in enhanced growth and biomass, increased cellulose production, improved fibre properties, improved digestibility by livestock, and increased yield properties as described in U.S. Pat. No. 6,184,440.

CBM Composition

When used for the applications described above, the CBM of the invention may be part of a composition made for the specific application. Further components in such compositions comprise a carrier compound, and one or more enzymes selected from the group consisting of proteases, cellulases, beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, other mannanases, pectin methylesterases, cellobiohydrolases, transglutaminases; or mixtures thereof.

Expression of the CBM of the Invention
Nucleic Acid Constructs Comprising Nucleotide Sequences The present invention relates to nucleic acid constructs comprising a nucleotide sequence of the invention operably linked to one or more control sequences that direct the expression of the coding sequence in a suitable host cell under conditions compatible with the control sequences.

A nucleotide sequence encoding a CBM of the invention may be manipulated in a variety of ways to provide for expression of the CBM. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al. (1978) Proceedings of the National Academy of Sciences USA 75:3727-3731), as well as the tac promoter (DeBoer et al. (1983) Proceedings of the National Academy of Sciences USA 80:21-25). Further promoters are described in "Useful proteins from recombinant bacteria" in Scientific American (1980) 242:74-94; and in Sambrook et al. (1989) supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al. (1992) Yeast 8:423-488.

The control sequence may also be a suitable transcription terminator sequence, a sequence recognized by a host cell to terminate transcription. The terminator sequence is operably linked to the 3' terminus of the nucleotide sequence encoding the CBM. Any terminator which is functional in the host cell of choice may be used in the present invention. Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al. (1992) supra.

The control sequence may also be a suitable leader sequence, a non-translated region of an mRNA which is important for translation by the host cell. The leader sequence is operably linked to the 5' terminus of the nucleotide sequence encoding the polypeptide. Any leader sequence that is functional in the host cell of choice may be used in the present invention. Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells a re obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman (1995) Molecular Cellular Biology 15:5983-5990.

The control sequence may also be a signal peptide coding region that codes for an amino acid sequence linked to the amino terminus of a polypeptide and directs the encoded CBM into the cell's secretory pathway. The 5' end of the coding sequence of the nucleotide sequence may inherently contain a signal peptide coding region naturally linked in translation reading frame with the segment of the coding region which encodes the secreted CBM. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the CBM. However, any signal peptide coding region which directs the expressed CBM into the secretory pathway of a host cell of choice may be used in the present invention. The native signal peptide coding region of the CBM of the present invention is nucleotides 10 to 69 of SEQ ID NO:1 encoding amino acids 1 to 20 of SEQ ID NO:2.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva (1993) Microbiological Reviews 57:109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Candida antarctica* lipase and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al. (1992) supra.

The control sequence may also be a propeptide coding region that codes for an amino acid sequence positioned at the amino terminus of a CBM. The resultant polypeptide may be denoted a pro-CBM or propolypeptide. A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Recombinant Expression Vector Comprising Nucleic Acid Construct

The present invention also relates to recombinant expression vectors comprising the nucleic acid construct of the invention. The various nucleotide and control sequences described above may be joined together to produce a recombinant expression vector, which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e. a vector which exists as an extrachromosomal entity, the replication of which is independent of chromosomal replication, e.g. a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome. For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by nonhomologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich (1978) Proceedings of the National Academy of Sciences USA 75:1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see e.g. Sambrook et al. (1989) supra).

Recombinant Host Cell Comprising Nucleic Acid Construct

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, such as a prokaryote or an non-unicellular microorganism, such as a eukaryote. Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen (1979) Molecular General Genetics 168:111-115), using competent cells (see, e.g., Young and Spizizin (1961) Journal of Bacteriology 81:823-829, or Dubnau and Davidoff-Abelson (1971) Journal of Molecular Biology 56:209-221), electroporation (see, e.g., Shigekawa and Dower (1988) Biotechniques 6:742-751), or conjugation (see, e.g., Koehler and Thorne (1987) Journal of Bacteriology 169:5771-5778).

The host cell may be a eukaryote, such as a mammalian, insect, plant, or fungal cell. In a preferred embodiment, the host cell is a fungal cell. "Fungi" as used herein includes the phyla Ascomycota, Basidiomycota, Chytridiomycota, and Zygomycota (as defined by Hawksworth et al. (1995) In, Ainsworth and Bisby's Dictionary of The Fungi, 8th edition, CAB International, University Press, Cambridge, UK) as well as the Oomycota (as cited in Hawksworth et al. (1995) supra) and all mitosporic fungi (Hawksworth et al. (1995) supra). In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore and Davenport, eds, (1980) Soc. App. Bacteriol. Symposium Series No. 9).

In an even more preferred embodiment, the yeast host cell is a *Candida*, *Hansenula*, *Kluyveromyces*, *Pichia*, *Saccharomyces*, *Schizosaccharomyces*, or *Yarrowia* cell. In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al. (1995) supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium*, *Aspergillus*, *Fusarium*, *Humicola*, *Mucor*, *Myceliophthora*, *Neurospora*, *Penicillium*, *Thielavia*, *Tolypocladium*, or *Trichoderma*. In a most preferred embodiment, the filamentous fungal host cell is an *Aspergillus awamori*, *Aspergillus foetidus*, *Aspergillus japonicus*, *Aspergillus nidulans*, *Aspergillus niger* or *Aspergillus oryzae* cell. In another most preferred embodiment, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In an even most preferred embodiment, the filamentous fungal parent cell is a *Fusarium venenatum* cell (*Nirenberg* sp. nov. such as the *Fusarium venenatum* deposited under Nos. CBS 458.93, CBS 127.95, CBS 128.95, CBS 148.95). In another most preferred embodiment, the filamentous fungal host cell is a *Humicola insolens*, *Humicola lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al. (1984) Proceedings of the National Academy of Sciences USA 81:1470-1474. Suitable methods for transforming *Fusarium* species are described by Malardier et al. (1989) Gene 78:147-156 and WO 96/00787. Yeast may be transformed using the procedures described by Becker and Guarente, In Abelson and Simon, eds, Guide to Yeast Genetics and Molecular Biology, Methods in Enzymology, Volume 194:182-187, Academic Press, Inc., New York; Ito et al. (1983) Journal of Bacteriology 153:163; and Hinnen et al. (1978) Proceedings of the National Academy of Sciences USA 75:1920.

Processes for Preparing Functional CBM's

The present invention also relates to methods for producing a CBM of the present invention comprising (a) cultivating a strain, which in its wild-type form is capable of producing the CBM; and (b) recovering the CBM. Preferably, the strain is a fungus, more preferably of the genus *Humicola*, particularly *Humicola insolens* or *Coprinus*, such as *Coprinus cinereus* or *Thielavia* such as *Thielavia terrestris* or *Aspergillus* such as *Aspergillus oryzae*.

The present invention also relates to a method for producing a CBM polypeptide, the method comprising the steps of
growing under conditions to overproduce CBM's in a nutrient medium *Aspergillus* host cells which have been transformed with an expression cassette which includes, as operably joined components,
a) a transcriptional and translational initiation regulatory region,
b) a DNA sequence encoding the CBM polypeptide,
c) a transcriptional and translational termination regulatory region, wherein the regulatory regions are functional in the host, and
d) a selection marker gene for selecting transformed host cells; and
recovering the CBM polypeptide.

In the production methods of the present invention, the cells are cultivated in a nutrient medium suitable for production of the CBM using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the CBM is secreted into the nutrient medium, the CBM can be recovered directly from the medium. If the CBM is not secreted, it can be recovered from cell lysates.

The produced CBM may be detected using methods known in the art and modifications thereof that are specific for the CBM. These detection methods may include use of specific antibodies or determination of binding to a carbohydrate substrate, such as Avicel®.

The resulting CBM may be recovered by methods known in the art. For example, the CBM may be recovered from the nutrient medium by conventional procedures including, but not limited to, centrifugation, filtration, extraction, spray-drying, evaporation, or precipitation. The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g. ammonium sulfate precipitation), SDS-PAGE, or extraction (see, e.g. Protein Purification, Janson and Ryden, eds (1989) VCH Publishers, New York).

Materials and Methods

Determination CBM Activity

A DNA sequence encoding a CBM from a given organism can be obtained conventionally by using PCR techniques, and, also based on current knowledge it is possible to find homologous sequences from other organisms.

It is contemplated that new CBM's can be found by cloning carbohydrate degrading enzymes such as cellulases, xylanases or other plant cell wall degrading enzyme and measure the binding to the target carbohydrate. Traditionally it has been assumed, that if the enzyme activity binds to the crystalline cellulose product Avicel® part of the gene codes for a cellulose-binding domain. The binding to Avicel® is tested under the standard conditions described below.

Cellulose affinity can be measured by using 10 g of Avicel® in a 500 ml buffered slurry (buffer: 0.1 sodium phosphate, pH 7.5) which is stirred slowly using a spoon and left swelling for 30 minutes at room temperature. Then the enzyme is added in a ratio of 1 part cellulose binding domain to 150 parts Avicel®. This is done on ice which gives optimum binding within 5 to 10 minutes. The Avicel® can then be washed and applied directly to SDS-PAGE for visualization of the bound proteins (since the use of SDS and cooking will release the bound proteins). Alternatively, the slurry is packed into a column and washed. The bound protein is eluted, either in ionized water or in a high pH buffer such as triethylamine (pH 11.2; 1% solution), where the pH eluted protein is quickly adjusted to neutral.

General Molecular Biology Methods

DNA manipulations and transformations are performed using standard methods of molecular biology as described in Sambrook et al., Molecular Cloning: A Laboratory Manual, Cold Spring Harbor Lab., Cold Spring Harbor, N.Y. (1989); Ausubel et al. (Eds.), Current Protocols in Molecular Biology, John Wiley and Sons (1995); Harwood and Cutting (Eds.) Molecular Biological Methods for *Bacillus*, John Wiley and Sons (1990).

Enzymes for DNA manipulations were used according to the specifications of the suppliers.

Example 1

Construction of an *Aspergillus* Expression Vector for a CBM Domain from *Pseudoplectania nigrella* which Domain was Secreted with a Family GH61 Enzyme Expression constructs of SEQ ID NO:1 were created by two different cloning procedures. The first procedure (A) uses inverse PCR to delete the enzymatic core of the family GH61 enzyme obtained from *Pseudoplectania nigrella*. Ligation of the product resulted in a plasmid containing the native secretion signal of the GH61 enzyme, fused in frame to the DNA encoding the carbohydrate-binding module. The second method (B) pursued for recombinant overexpression of the CBM of the invention was to clone the DNA encoding the CBM domain into a vector containing a *Candida* lipase signal peptide.

A—Inverse PCR

Primers NP887U1 and NP887D1 were synthesized as 5' phosphorylated primers. Amplification of plasmid DNA encoding the full open reading frame (ORF) of the family GH61 enzyme was used as template. The OFR can be obtained from the deposited strain CBS 444.97 by use of primers NP887U1 and NP887D1. Approximately 100 nanograms of DNA were used as template in a PCR reaction with the two primers A and B.

NP887U1
5'-GACATCGTTGACGGAGAGTCCGTAGACACGA- (SEQ ID NO: 3)
3'

NP887D1
5'-ACATCCTCCGGCACCTCCAATGACAAGGCCGTC (SEQ ID NO: 4)
G-3'

The protocol followed was the basic protocol of the Excite PCR mutagensis as described in the Stratagene (USA) user manual Catalogue number 200502.

| Component | |
|---|---|
| dH$_2$O | 32.75 µl |
| 10× PfuUltra buffer | 5.0 µl |
| dNTPs (10 mM stock) | 1.25 µl |
| NP887U1 (100 pMol/µl) | 5.0 µl |
| NP887D1 (100 pMol/µl) | 5.0 µl |

1 µl of PfuUltra (Stratagene, USA) was added to the reaction and then the sample was placed in a thermal cycler under the following conditions:

| 95 degrees Celsius | 2 min |
|---|---|
| followed by 20 cycles of | |
| 95 degrees Celsius | 2 minutes |
| 55 degrees Celsius | 30 seconds |
| 72 degrees Celsius | 7 minutes |

5 µl of the PCR reaction was removed for agarose gel analysis to confirm amplification of a band of the expected size (ca. 6 Kb). To the remaining 45 µl, 40 units of DpnI restriction enzyme were added. The sample was returned to the thermal cycler and incubated at 37 degrees Celsius for 30 minutes followed by 65 degrees Celsius for 30 minutes. The treated sample was purified by the GFX column purification kit according to the manufacturer's instructions (Amersham Biosciences, USA).

| treated PCR sample | 9 µl |
|---|---|
| 10× ligation buffer | 1 µl |
| 0.5 µl New England Biolabs T4 DNA ligase | |
| (ca. 200 NEB cohesive end units) | |

The ligation was performed at 17 degrees Celsius overnight and then transformed into TOP10 Chemically competent cells according to the manufacturers instructions. The transformation was plated out on LB agar with 50 mg/liter ampicillin. Eleven of the several hundred colonies that grew were miniprepped (Qiaspin® columns, Qiagen Ltd.) and the DNA cut with EcoRI and NotI to liberate the insert. Eight out of the eleven plasmids had an insert of the correct size (ca. 700 bp). The insert was sequenced for these plasmids containing inserts. The colonies were sequenced with vector primer PNA2I (5'-GTT TCC AAC TCA ATT TAC CTC-3' SEQ ID NO:5). It was determined that no errors were introduced in any of the insert sequences as a result of PCR. Of the eight plasmids pCBMX-K1 was chosen for a medium scale Jet-Star® (GENOMED, Germany) plasmid preparation from 100 µl of LB ampicillin grown plasmid containing E coli cells.

The DNA sequence of the fusion construction of pCBMX-K1, and the corresponding amino acid sequence, are shown in SEQ ID NO:1 and SEQ ID NO:2, respectively.

Transformation of Construct pCBMX-K1 into *Aspergillus Oryzae*

The DNA of SEQ ID NO:1 was transformed into *Aspergillus oryzae* strain JAL355 (disclosed in international patent application WO 01/98484A1). Transformants of SEQ ID NO:1 was re-isolated twice under selective and non-inducing conditions on Cove minimal plates (Cove (1966) Biochim. Biophys. Acta 133:51-56) with 1M sucrose as a carbon source and 10 mM nitrate. To test expression of SEQ ID NO:1, transformants were grown for 3 days and 4 days at 30 degrees Celsius in tubes with 10 ml YPM (2% peptone, 1% yeast extract, 2% maltose). Supernatants were run on NuPage® 10% Bis-Tris SDS gels (Invitrogen, USA) as recommended by the manufacturer. All *Aspergillus* isolates grew well even when induced for the expression of the DNA of SEQ ID NO:1.

B—Construction and Expression of CBM Using a *Candida Antartica* Lipase Signal Peptide The second method pursued for recombinant overexpression of the CBM domain of the invention was to clone the CBM domain into a specially prepared vector containing the necessary *Aspergillus* regulatory elements (promoter, terminator, etc.) and a signal peptide with signal cleavage site of a secreted lipase gene from *Candida antarctica*. Cloning of the PCR product consisting of the CBM domain into the vector allows for an in frame fusion of the CBM domain with the signal peptide. Expression of the construct in *Aspergillus oryzae* should result in efficient secretion of the enzyme due to the presence of the provided secretion signal and cleavage site. The vector used, pDau109 is a derivative of pJAL721, which is described in WO 03/008575.

The plasmid pDau109 differs from pJaL721 in that the ampicillin resistance gene has been inserted into the pyrG selectable marker. The improvements made in pDau109 vector are first, the selection marker URA3 of *E. coli* that has been replaced by a URA3 gene disrupted by the insertion of the ampicillin resistance gene *E. coli* beta lactamase. This feature allows for facile selection for positive recombinant *E. coli* clones using commercially available and highly competent strains on commonly used LB ampicillin plates. Furthermore the Ampicillin resistance gene is entirely removable using the two flanking NotI sites restoring a functional selection marker URA3. In addition, pDau109 has a *Candida antarctica* lipase (SWALL:LIPB_CANAR) signal sequence (amino acids 1-57 of SEQ ID NO:9) and cleavage site introduced after the fungal promoter in which a number of convenient cloning sites are available for in frame fusions of a supplied coding region with the *C. antarctica* secretion signal. Specifically, pDau109 has 8 unique restriction sites that can be used to insert a cDNA (BstXI-FspI-SpeI-NruI-XcmI-HindIII-XhoI). Standard methods were used for modification of pJaL724 into pDau109.

Plasmid of pDau109 was prepared by medium scale Qiagen® midi plasmid preparation (Qiagen) from 100 mls of LB ampicillin grown plasmid containing *E. coli* cells.

Generation of the CBM Domain with HindIII Sites

The following primers were used in a standard PCR reaction, the HindIII restriction sites introduced for cloning purposes are underlined:

NP887Dau1
5'-<u>CCAAAGCTTT</u>TCATCCTCCGGCACCTCCAATG- (SEQ ID NO: 6)
3'

-continued

NP887Dau2
5'-GCGAAGCTTAATCTTACTCCATCTCACCTCCC-3' (SEQ ID NO: 7)

Plasmid NP887-1 encoding the GH61 coding region was used as PCR template.

| pNP887 DNA (100 ng) | 1 µl |
| 10× ProofStart buffer | 5 µl |
| dNTP 20 mM | 0.75 µl |
| NP887Dau1(100 pMol/µl) | 0.5 µl |
| NP887Dau2(100 pMol/µl) | 0.5 µl |
| H$_2$O | 41.25 µl |
| ProofStart ® DNA polymerase (Qiagen Ltd) | 1 µl |
| The sample was transferred to a thermal cycler and the following program run: | |
| 95 degrees Celsius | 5 min |
| Then 20 cycles of | |
| 94 degrees Celsius | 30 seconds |
| 60 degrees Celsius | 30 seconds |
| 72 degrees Celsius | 1 minute |

Five µl of the PCR reaction was inspected on an Agarose gel and a band corresponding to the correct size (ca. 500 bp) was observed. The remaining 45 µl of sample was purified by the GFX purification method (Amersham Biosciences). The sample was then restricted with HindIII under standard conditions (40 units/µg DNA, 37 degrees Celsius) overnight. The treated fragment (NP887-CBM) was once more GFX purified and stored at –20 degrees Celsius until further use.
Preparation of pDau109 pDau109 plasmid DNA was restricted with HindIII for four hours under standard conditions. 10 units of Shrimp Alkaline Phosphatase was added to the reaction and the incubation at 37 degrees Celsius continued for an additional 2 hours. The sample was then heat treated at 65 degrees Celsius for 20 minutes to inactivate the enzyme. The treated plasmid was GFX purified and stored at –20 degrees Celsius until later use.

| Ligation | |
| --- | --- |
| Vector pDau109 HindIII* | 1 µl (ca. 90 ng) |
| NP887-CBM PCR frag-HindIII | 7 µl |
| T4 DNA ligase buffer (NEB) | 1 µl |
| NEB T4 DNA ligase | 0.3 µl |

The ligation was performed at 16 degrees Celsius overnight and then stored in –20 degree Celsius until used.
Transformation The ligation was performed at 16 degrees Celsius overnight and then transformed into TOP10 Chemically competent cells according to the manufacturers instructions. The transformation was plated out on LB agar with 50 mg/liter ampicillin. Twelve of the several hundred colonies that grew were miniprepped (Qiaspin® columns, Qiagen Ltd.) and the DNA cut HindIII to liberate the insert. Four out of the twelve plasmids had an insert of the correct size (ca. 500 bp). The plasmids containing inserts were sequenced with vector primer PNA21 (SEQ ID NO:5) to determine integrity and orientation of the insert. It was determined that no errors were introduced in any of the insert sequences as a result of PCR. Plasmid pCBMX-S1 was found to be error free and in the correct orientation and was therefore chosen for a medium scale Qiagen® midi plasmid preparation (Qiagen) from 100 µl of LB ampicillin grown plasmid containing *E. coli* cells. The DNA sequence of the fusion construct pCBMX-S1, and the corresponding amino acid sequence, are shown in SEQ ID NO:8 and SEQ ID NO:9, respectively.

Transformation of Construct pCBMX-S1 into *Aspergillus Oryzae*:

The fusion construct pCBMX-S1 (SEQ ID NO:8) was transformed into *Aspergillus oryzae* strain BECh2, which was constructed as described in WO 00/39322 (BECh2 is derived from strain *Aspergillus oryzae* JaL228, which is constructed on the basis of the deposited strain *Aspergillus oryzae* IFO 4177 as described in WO 98/12300).

Transformation media AMDS media:

| Agarose | 20 g |
| Cove salt | 20 ml (Cove (1966) supra) |
| Sucrose | 342 g |
| dH2O | to 100 ml |
| autoclave at 121 degrees Celsius for 20 minutes allow to cool then add: | |
| 1M acetamide | 10 ml |
| 1M CsCl | 15 ml |

AMDS media for re-isolation of transformants: The same as above but without added CsCl and adding 100 µl triton-X100 per 1000 ml media.

Transformants of pCBMX-S1 were re-isolated twice on Cove sucrose media (Cove (1966) Biochim. Biophys. Acta 133:51-56) with 1M sucrose as a carbon source and 10 mM nitrate. To test expression of the fusion construct pCBMX-S1, which contains the *Candida antarctica* lipase (SWALL:LIP-B_CANAR) signal sequence and the *P. nigrella* CBM polypeptide of the invention (SEQ ID NO:8), 23 transformants were grown for 3 days and 4 days at 30 degrees Celsius in tubes with 10 ml YPG (2% peptone, 1% yeast extract, 2% glucose). Supernatants were run on NuPage® 10% Bis-Tris SDS gels (Invitrogen, USA) as recommended by the manufacturer. SYPRO® Orange Gel staining was used according to the manufacturer's instructions (Molecular Probes, USA). Three of the isolates revealed a diffuse band between 35-45 kDa on the SDS gel. These were analyzed further with various 150 ml shake flask media fermentations. 1000 ml Erlenmeyer flasks with side baffles was used with 150 mls of each of 4 different media:

YPM: 2% peptone, 1% yeast extract, 2% maltose
YPG: 2% peptone, 1% yeast extract, 2% glucose
DAP2C: For 1 liter media; MgSO4.7H2O (Merck 5886) 1 g, KH2PO4 (Merck 4873) 1 g, Citric Acid (Merck 244) 2 g, Maltodextrin (Roquette), K3PO4.H2O 5.2 g, Yeast extract (Difco 0127) 0.5 g, AMG spore metals 0.5 mls (Zink Chloride: Merck 8816, 6.8 g; Copper Sulphate: Merck 2790, 2.5 g; Nickel Chloride: Merck 6717, 0.24 g; Iron sulphate: Merck 3965, 13.9 g; Manganese sulphate: Merck 5941, 8.45 g; Citric acid: Merck 0244, 3 g), Pluronic® PE 6100 (BASF).
FG4P: 3% Soybean meal (SFK 102-2458), 1.5% Maltodextrin (Roquette), 0.5% Peptone bacto (Difco 0118), 1.5% KH2PO4 (Merck 4873), 0.2 mls/liter Pluronic® PE 6100 (BASF).

A heavy inoculum of several thousand spores was used for each and the shake flasks were agitated on an orbital shaker at 150 RPM at 30 degrees C.

*Aspergillus* isolates grew well even when induced for the expression of the CBM polypeptide of the invention.

Example 2

Purification of SEQ ID NO:9 from Expression of SEQ ID NO:8 in *Aspergillus*

The *Aspergillus oryzae* strain described in Example 1B expressing the CBM (CBMX) of the *Pseudoplectania* nigrella GH61 with *Candida antarctica* lipase signal peptide was grown in shake flasks. About 1 liter culture broth was sterile filtered and the filtrate loaded onto a column containing 50 g Avicel®. Non-binding and weakly binding proteins were removed by washing with Milli-Q® water. Proteins with affinity for Avicel® were eluted with 0.1 M Tris, pH 11.5. Immediately after elution, pH of this Avicel®-binding fraction was adjusted to 7.5, and the fraction was concentrated using an Amicon® cell (Millipore®, USA) with a membrane having a cut-off of 6 kDa. On SDS-PAGE the majority of the protein binding to Avicel® appeared as a broad band of molecular weight 35-45 kDa, which is considerably higher than the molecular weight of the protein part of the carbohydrate binding module. The high and heterogeneous molecular weight is probably due to heterogeneity in O- and N-glycosylation of the N-terminal part of the protein. N-terminal sequencing of the 35-45 kDa band gave exclusively the sequence SFSSSGT (positions 47-53 of SEQ ID NO:9) indicating that heterogeneity in the N-terminal amino acid sequence is not present.

Example 3

Specificity of Binding of Purified CBMX

The carbohydrate-binding domain with affinity for Avicel® and purified as described in Example 2 (CBMX) was studied further. 50 µl purified CBMX was mixed with 500 µl 20 mM Tris, pH 7.5 containing varying amount of Avicel® (0-100 mg/ml) in an Eppendorf tube. After 4 hours incubation at room temperature with agitation, the samples were centrifuged. 200 µl supernatant was transferred to the well of a microtiter plate (Costar, UV plate) and absorbance read at 280 nm on a microtiter plate reader (SpectraMax® Plus, Molecular Devices). The results in Table 1 indicate that the large majority of the protein binds to the highest concentrations of Avicel®.

TABLE 1

Binding of CBMX to Avicel ®. A280: Absorbance at 280 nm of 200 µl supernatant in microtiter plate with absorbance of buffer and Avicel subtracted.

| Avicel ® (mg/ml) | A280 |
|---|---|
| 100 | 0.0095 |
| 50 | 0.0185 |
| 25 | 0.0326 |
| 12.5 | 0.0540 |
| 6.25 | 0.0637 |
| 3.125 | 0.0729 |
| 1.563 | 0.0799 |
| 0.781 | 0.0808 |
| 0.391 | 0.0777 |
| 0.0 | 0.0768 |

Experiments with shorter incubation time (15 min to 1 hour) gave less complete binding.

A similar binding study was performed with PASO (Phosphoric Acid Swollen Cellulose: To 5 g Avicel® moistened with water 150 ml ice-cold 85 ortho-phosphoric acid is added. After 1 hour stirring on ice bath, 500 ml cold acetone is added. The suspension is filtered and washed, first with acetone and then with water). 50 µl purified CBMX was mixed with 500 µl 20 mM Tris, pH 7.5 containing varying amount of PASO (0-10 mg/ml) in an Eppendorf tube. Samples were incubated 4 hours at room temperature with agitation. After centrifugation, 200 µl supernatant was transferred to the well of a microtiter plate and absorbance read at 280 nm. The results in Table 2 show that increasing amount of PASO reduces the amount of absorbance of CBMX in the supernatant, i.e. CBMX has affinity for PASO.

TABLE 2

Binding of CBMX to PASC. A280: Absorbance at 280 nm of 200 µl supernatant in microtiter plate with absorbance of buffer subtracted.

| PASC (mg/ml) | A280 |
|---|---|
| 10 | 0.0471 |
| 5 | 0.0512 |
| 2.5 | 0.0618 |
| 1.25 | 0.0710 |
| 0.625 | 0.0682 |
| 0.0 | 0.0753 |

Affinity of CBMX for a number of soluble carbohydrates was tested in a competition assay by mixing 100 µl CBMX with both Avicel® (400 µl 50 mg/ml in 20 mM Tris, pH 7.5) and the soluble carbohydrate (dissolved in 500 µl 20 mM Tris, pH 7.5). As references, samples without CBMX or soluble carbohydrate added were used. If CBMX has affinity for the soluble carbohydrate it should be able to keep CBMX in solution which can be measured as increase in absorbance at 280 nm compared to sample without soluble carbohydrate added. After 4 hours incubation at room temperature with agitation, samples were centrifuged and absorbance at 280 nm was read using 200 µl supernatant in the well of a microtiter UV plate.

Tested soluble carbohydrates were barley β-glucan (Megazyme, low viscosity), lichenan (Megazyme, Icelandic moss), CMC (carboxymethyl cellulose 7LF, Hercules, USA), Xyloglucan (Megazyme, amyloid, from tamarind seed), lupin galactan (Megazyme) and Locust bean gum (Sigma, G-0753).

From the results in Table 3 it is seen that beta-glucan and CMC are able to keep almost all CBMX in solution. Also locust bean gum keeps the majority in solution, whereas xyloglucan and galactan result in about half of the CBMX in solution. Addition of lichenan does not result in any increase in CBMX in solution. These results indicate affinity of CBMX for beta-glucan, CMC and locust bean gum and to some extent also for xyloglucan and galactan, whereas no affinity for lichenan could be detected.

TABLE 3

Competition binding assay with CBMX, Avicel ® (20 mg/ml) and soluble carbohydrates. Concentration of carbohydrate: Concentration of soluble carbohydrate during incubation with CBMX and Avicel ®. Difference in A280: Difference in absorbance at 280 nm between samples with and without CBMX added.

| Soluble carbohydrate | Carbohydrate conc. (mg/ml) | Difference in A280 |
|---|---|---|
| None - Only Avicel ® and CBMX | | 0.018 |
| None - Only CBMX | | 0.108 |
| beta-Glucan | 20 | 0.100 |
| Lichenan | 20 | 0.025 |
| CMC | 25 | 0.129 |
| Xyloglucan | 11 | 0.052 |
| Galactan | 20 | 0.043 |
| Locust bean gum | 25 | 0.087 |

The invention claimed is:

1. An enzyme hybrid comprising a carbohydrate-binding module and a catalytic domain exhibiting enzyme activity, wherein the carbohydrate-binding module is heterologous to the catalytic domain exhibiting enzyme activity and wherein the carbohydrate-binding module has at least 90% identity with the sequence of amino acids 34-174 of SEQ ID NO:2.

2. The enzyme hybrid of claim 1, wherein the catalytic domain exhibits endo-beta-1,4-glucanase activity.

3. The enzyme hybrid of claim 1, wherein the catalytic domain exhibiting enzyme activity is an enzyme selected from the group consisting of an acetyl xylan esterase, alpha-L-arabinofuranosidase, amylase, arabinase, beta-glucosidase, beta-mannosidase, beta-1,3-1,4-glucanase, cellulase, cellulose 1,4-cellobiosidase, cellobiohydrolase, cinnamoyl esterase, endo-1,4-beta-xylanase, endo-1,4-galactanase, pectinase, exo-polygalacturonase, feruloyl esterase, glucan 1,3-beta-glucosidase, licheninase, lipase, mannan endo-1,4-mannosidase, oxidoreductase, pectin methylesterase, pectin acetylesterase, phenol-oxidizing oxidase, polygalacturonase, protease, rhamnogalacturonase, rhamnogalacturonan acetyl esterase, rhamnogalacturonan hydrolase, rhamnogalacturonan lyase, rhamnogalacturonan methyl esterase, xylanase, xyloglucanase, and xylan methyl esterase.

4. The enzyme hybrid of claim 1, wherein the carbohydrate-binding module has at least 95% identity with the sequence of amino acids 34-174 of SEQ ID NO: 2.

5. The enzyme hybrid of claim 1, wherein the carbohydrate-binding module has at least 97% identity with the sequence of amino acids 34-174 of SEQ ID NO: 2.

6. The enzyme hybrid of claim 1, wherein the carbohydrate-binding module is a fragment of the sequence of amino acids 34-174 of SEQ ID NO: 2, which retains carbohydrate-binding module activity.

7. The enzyme hybrid of claim 1, wherein the carbohydrate-binding module comprises the sequence of amino acids 34-174 of SEQ ID NO: 2.

8. The enzyme hybrid of claim 7, wherein the carbohydrate-binding module is encoded by a DNA sequence obtained from *Pseudoplectania nigrella* CBS 444.97.

9. A detergent composition comprising an enzyme hybrid of claim 2 and a surfactant.

10. A method of finishing a textile, comprising treating the textile with an enzyme hybrid of claim 2.

11. A method of baking a baking product, comprising
 (a) adding an enzyme hybrid of claim 2 to either a flour that is then used to form a dough or directly to a dough; and
 (b) baking the dough to form the baked product.

12. A method for degradation of cellulose-containing biomass, comprising treating the biomass with an effective amount of an enzyme hybrid of claim 2.

* * * * *